United States Patent
Hoeholt et al.

(10) Patent No.: US 9,675,761 B2
(45) Date of Patent: Jun. 13, 2017

(54) DRUG DELIVERY DEVICE WITH VARIABLE DOSE SETTING MECHANISM

(71) Applicant: Novo Nordisk A/S, Bagsvaerd (DK)

(72) Inventors: Jesper Hoeholt, Melby (DK); Michael Monrad, Frederiksberg (DK); Carsten Schau Andersen, Valby (DK); Mikkel Schouenborg Grubbe, Hilleroed (DK); Bennie Peder Smiszek Pedersen, Haslev (DK)

(73) Assignee: Novo Nordisk A/S, Bagsvaerd (DK)

( * ) Notice: Subject to any disclaimer, the term of this patent is extended or adjusted under 35 U.S.C. 154(b) by 126 days.

(21) Appl. No.: 14/441,032

(22) PCT Filed: Nov. 19, 2013

(86) PCT No.: PCT/EP2013/074133
§ 371 (c)(1),
(2) Date: May 6, 2015

(87) PCT Pub. No.: WO2014/076289
PCT Pub. Date: May 22, 2014

(65) Prior Publication Data
US 2015/0297835 A1    Oct. 22, 2015

Related U.S. Application Data

(60) Provisional application No. 61/729,757, filed on Nov. 26, 2012.

(30) Foreign Application Priority Data

Nov. 19, 2012  (EP) ..................................... 12193146

(51) Int. Cl.
*A61M 5/00*   (2006.01)
*A61M 5/315*  (2006.01)
(Continued)

(52) U.S. Cl.
CPC .......... *A61M 5/31551* (2013.01); *A61M 5/24* (2013.01); *A61M 5/31528* (2013.01);
(Continued)

(58) Field of Classification Search
CPC ...... A61M 2205/6018; A61M 5/31553; A61M 2005/3125; A61M 2205/6036;
(Continued)

(56) References Cited

U.S. PATENT DOCUMENTS

| | | | |
|---|---|---|---|
| 6,585,698 B1* | 7/2003 | Packman | ................ A61M 5/24 604/207 |
| 2004/0210199 A1 | 10/2004 | Atterbury et al. | |
| 2011/0172640 A1* | 7/2011 | Cronenberg | ...... A61M 5/31555 604/506 |

FOREIGN PATENT DOCUMENTS

| | | |
|---|---|---|
| EP | 1095668 A1 | 5/2001 |
| WO | 2012022771 A2 | 2/2012 |
| WO | 2012089620 A2 | 7/2012 |

* cited by examiner

*Primary Examiner* — Emily Schmidt
(74) *Attorney, Agent, or Firm* — Wesley Nicolas

(57) ABSTRACT

A drug delivery system (1) comprising first (35) and second reservoir units (30) with first and second identifiers (32), and a main unit (10) adapted to receive either of the first (35) and second reservoir units (30) in a mounted position. The main unit (10) comprises drug expelling means having dose setting means (11, 1, 14, 15, 19) comprising a rotational dose setting member allowing a user to set a desired dose size for the given drug, the dose size being set in fixed increments for a given state. The drug expelling means has a first state in which an increment corresponds to a first volume of drug, and a second state in which an increment corresponds to a second volume of drug, wherein the drug expelling means is set in the first state by means of the first identifier when a first reservoir unit is mounted, and the drug expelling means
(Continued)

is set in the second state by means of the second identifier when a second reservoir unit is mounted.

11 Claims, 3 Drawing Sheets

(51) Int. Cl.
*A61M 5/24* (2006.01)
*A61M 5/31* (2006.01)

(52) U.S. Cl.
CPC . *A61M 5/31553* (2013.01); *A61M 2005/2407* (2013.01); *A61M 2005/3126* (2013.01); *A61M 2202/0007* (2013.01); *A61M 2205/43* (2013.01); *A61M 2205/50* (2013.01); *A61M 2205/6036* (2013.01); *A61M 2205/6045* (2013.01)

(58) Field of Classification Search
CPC .. A61M 2205/6045; A61M 2005/3126; A61M 5/3156; A61M 5/3155; A61M 5/31545; A61M 5/31526
See application file for complete search history.

DRUG DELIVERY DEVICE WITH VARIABLE DOSE SETTING MECHANISM

CROSS-REFERENCE TO RELATED APPLICATIONS

This application is a 35 U.S.C. §371 National Stage application of International Application PCT/EP2013/074133 (published as WO 2014/076289), filed Nov. 19, 2013, which claims priority to European Patent Application 12193146.3, filed Nov. 19, 2012; this application claims priority under 35 U.S.C. §119 to U.S. Provisional Application 61/729,757; filed Nov. 26, 2012.

The present invention generally relates to medical delivery devices adapted for transcutaneous delivery of an amount of drug.

BACKGROUND OF THE INVENTION

In the disclosure of the present invention reference is mostly made to the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. Modern devices have become more sophisticated and often include diverse and robust functions, such as memories for remembering time and amount of last dose, as well as, in the case of insulin devices, blood glucose monitors. While pen-style injection devices are typically cylindrically shaped with a needle protruding from the most distal portion of one end of the device, some devices have other shapes with the needle no longer protruding from the most distal part of an end of the device, e.g. Innovo® and InnoLet® from Novo Nordisk A/S, Bagsvaerd, Denmark.

Typically, injection devices use a pre-filled cartridge containing the medication of interest, e.g. 1.5 or 3.0 ml of insulin or growth hormone. The cartridge is typically in the form of a generally cylindrical transparent ampoule with a needle pierceable septum at one end and an opposed piston designed to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded. Most injection devices are provided with a releasable pen cap covering and protecting the cartridge, the needle mount portion with the pierceable septum, and, as may be the case, a mounted needle. To protect the needle it is normally provided with an inner needle cap.

Normally insulin formulations are provided with a concentration of 100 IU/ml, i.e. 300 UI in a 3 ml cartridge. This said, it may be desirable to provide a given drug in different concentrations, e.g. a given type of insulin may be provided in cartridges having a concentration of either 100 IU/ml or 200 IU/ml, the latter providing that for a given dose amount of active drug only half the volume has to be delivered.

WO 2012/022771 discloses an electronically controlled drug delivery system adapted to detect a property of a cartridge. The property may be drug concentration allowing the system to vary the volume of drug dispensed to allow for varying drug concentration. EP 1 095 668 discloses an electronically controlled drug delivery system adapted to detect the diameter of a cartridge and calculate the distance the piston has to be advanced in order to expel a given amount of drug.

However, disregarding electronically controlled infusion pumps which may be set in accordance with drug concentration, traditional mechanical drug delivery devices are designed to expel a fixed volume of drug for each increment of the dose setting mechanism, e.g. a set insulin dose of 30 IU will result in 0.3 ml of insulin formulation to be expelled. Correspondingly, a specifically adapted drug expelling device would have to be provided for each concentration of drug just as it has to be ensured that a given drug cartridge cannot be used in the wrong device.

Having regard to the above, it is an object of the present invention to provide a drug delivery system having a mechanical expelling mechanism and which in a cost-effective manner allows a given drug to be supplied in cartridges having different concentrations. The device should be simple, safe and convenient to use.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect a drug delivery system is provided comprising a first reservoir unit comprising a first drug formulation of a given drug having a first concentration, and a first mechanical identifier corresponding to the first drug formulation, and a second reservoir unit comprising a second drug formulation of the given drug having a second concentration, and a second mechanical identifier corresponding to the second drug formulation. The system further comprises a main unit comprising mounting means allowing either of the first and second reservoir units to be mounted relative to the main portion, drug expelling means for expelling drug from a mounted reservoir unit corresponding to a set dose size, and dose setting means comprising a rotational dose setting member allowing a user to set a desired dose size for the given drug, the dose size being set in fixed increments for a given state. In such a system the drug expelling means has a first state in which an increment corresponds to a first amount of angular displacement of the dose setting member corresponding to a first volume of drug, and a second state in which an increment corresponds to a second amount of angular displacement of the dose setting member corresponding to a second volume of drug. Further, the drug expelling means is set in the first state by means of the first identifier when a first reservoir unit is mounted, and the drug expelling means is set in the second state by means of the second identifier when a second reservoir unit is mounted.

By the above arrangement a main unit (e.g. in the form of a drug delivery device) is provided in which a cartridge-controlled settable mechanical drug expelling mechanism ensures that a user can set a dose for either of two concentrations of drug by essentially rotating a dose setting member as in a traditional drug delivery device. In this way the user is provided with a drug delivery device which is simple, safe and convenient to use by essentially resembling a conventional device.

The increments of the first and second states may correspond to the first and second concentration of drug, such that for a given number of increments the same amount of active drug is expelled.

In exemplary embodiments the dose setting means comprises a ratchet mechanism settable in the first and second fixed increments, the ratchet mechanism having a first and a second state corresponding to the first and second state of the expelling mechanism.

The ratchet mechanism may comprise a first ratchet ring having a first increment size, a second ratchet ring having a second increment size, a coupling ring having a first ratchet portion facing the first ratchet ring and having the first increment size, and a second ratchet portion facing the second ratchet ring and having the second increment size. In such a mechanism the coupling means may have a first and a second state corresponding to the first and second state of the expelling mechanism is provided, wherein the coupling ring and the second ratchet ring is rotationally locked to each other in the first state, this providing a ratchet having the first increment size, and wherein the coupling ring and the first ratchet ring is rotationally locked to each other in the second state, this providing a ratchet having the second increment size.

In the above disclosure of the invention first and second reservoir units with first and second concentrations and corresponding first and second identifiers are described, however, the system may comprise further reservoir units with further concentrations and identifiers.

The mounting means allowing a reservoir unit to be mounted relative to the main portion may be in the form of a traditional detachable rear-loaded cartridge holder, or a non-detachable front-loaded cartridge holder. A reservoir unit may alternatively be supplied pre-mounted in a disposable cartridge holder, the main portion mounting means being in the form of coupling means allowing the reservoir unit to be attached directly. In the latter case the identifier may be formed as part of the disposable cartridge holder portion.

The main unit may be provided with display means adapted to display a drug dose amount in the same fixed increments for each of the first and second drug formulations, e.g. 1 IU of insulin.

In an exemplary embodiment the dose setting means comprises a rotatable dose setting member which can be set in fixed increments of a given drug amount, e.g. 1 IU of insulin, when the drug expelling means is in either the first or second state, wherein the amount of rotation per increment varies according to the set state. The dose setting member may be operationally coupled to display means in the form of first and second rotatable scales, the first scale being viewable when the expelling means is in the first state, and the second scale being viewable when the expelling means is in the second state, e.g. in form of a rotatable drum member operationally coupled to the dose setting member, the first and second scale being arranged on the drum member.

Alternatively the main unit may be provided with processor means, an electronically controlled display, and encoder means operationally coupled to the dose setting member. In such an arrangement the encoder means can be set in a first state by means of the first identifier when a first reservoir unit is mounted, and the encoder means can be set in a second state by means of the second identifier when a second reservoir unit is mounted, whereby a set drug dose amount is displayed in the same fixed increments, e.g. 1 IU of insulin, for each of the first and second drug formulations.

The drug delivery system may further comprise signal generating means adapted to generate, for a given state, a tactile and/or audible signal for each increment during setting of a dose. The drug expelling means may be driven manually, by a manually actuated spring, or a pre-energized spring.

The main unit may be provided with signal generating means adapted to generate (for a given state) a tactile and/or audible signal for each increment during setting of a dose. For example, a "click" sound may be generated for each increment. The sound may be generated by an inherent component of the expelling mechanism, e.g. by a ratchet mechanism, or by a separate mechanism.

As used herein, the term "drug" is meant to encompass any drug-containing flowable medicine capable of being passed through a delivery means such as a cannula or hollow needle in a controlled manner, such as a liquid, solution, gel or fine suspension. Representative drugs include pharmaceuticals such as peptides (e.g. insulins, insulin containing drugs, GLP-1 containing drugs as well as derivates thereof), proteins, and hormones, biologically derived or active agents, hormonal and gene based agents, nutritional formulas and other substances in both solid (dispensed) or liquid form. In the description of the exemplary embodiments reference will be made to the use of insulin containing drugs.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only. When the terms member or element is used for a given component it generally indicates that in the described embodiment the component is a unitary component, however, the same member may alternatively comprise a number of sub-components just as two or more of the described components could be provided as unitary components, e.g. manufactured as a single injection moulded part.

Figure 1:
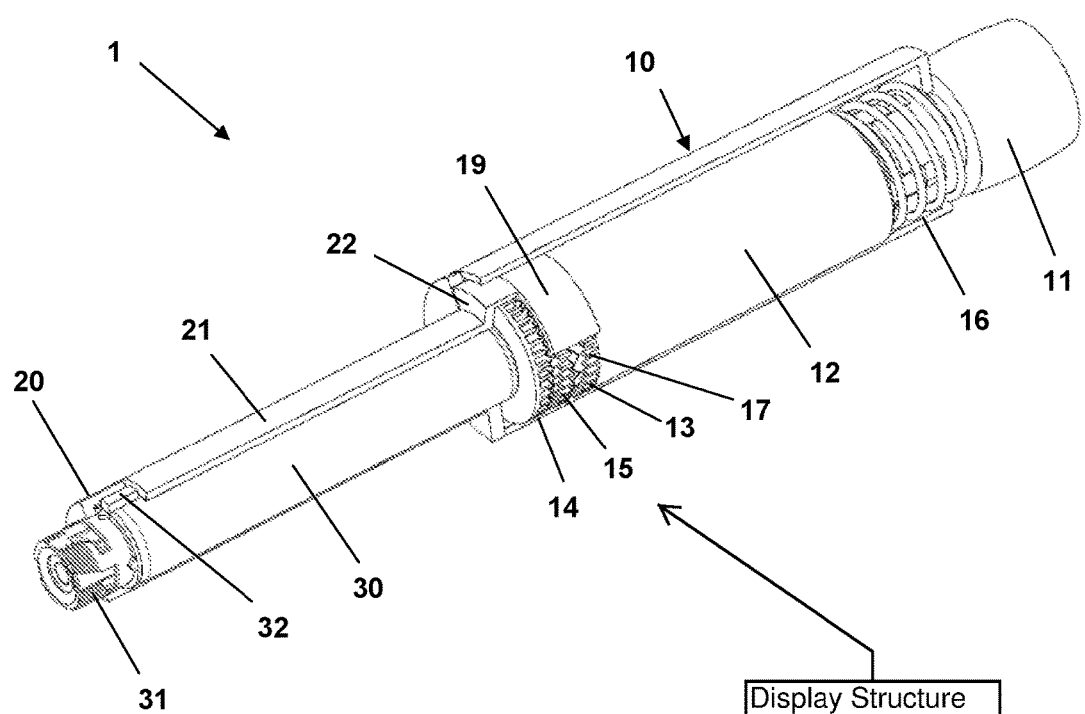
FIG. 1 shows a drug delivery device with a ratchet mechanism.

Referring to FIG. 1 a drug delivery device 1 will be described. The shown device can be considered a "demonstrator" showing mainly only those elements necessary for illustrating and understanding the present invention.

The device comprises a main (or body) part 10 with a rotational proximal dose setting member 11 and a distal cartridge holder 20 for receiving and holding a drug-filled cartridge (or reservoir) 30 with an axially displaceable piston (not shown) and a distal outlet with an associated needle mount 31 adapted to allow a needle assembly to be mounted in fluid communication with the reservoir. In the shown embodiment an identifier 32 is formed as part of the needle mount, see below. The needle mount may be part of either the cartridge as in the shown embodiment or the structure for holding the cartridge. The main part is provided with drug expelling means comprising user actuatable dose setting means as well as drive means having an axially displaceable piston rod for moving the piston distally to thereby expel a user-settable dose of drug from the reservoir. In the shown embodiment the drive means (not shown) comprises a spring which is energized during dose setting and subsequently released to drive the piston rod distally, such a design allowing the dose setting member to not move axially during dose setting. The drive means may have any configuration suitable for driving, either automatically or manually, a piston rod distally to an extent corresponding to a user-set dose as determined by the actual set state of the dose setting means.

Turning to the embodiment of FIG. 1, the dose setting means comprises a ratchet mechanism having a cylindrical ratchet member 12 with a distal ratchet ring 13 formed integrally therewith and having a distally facing ratchet surface comprising a first number of teeth, e.g. 24 in the shown embodiment. The ratchet member is rotationally coupled to the dose setting member 11 and allowed to move slightly axially. The ratchet mechanism further comprises a distal stationary ratchet ring 14 formed integrally with the cartridge holder and comprising a proximally facing ratchet surface with a second number of teeth, e.g. 48 in the shown embodiment. Between the two ratchet surfaces an axially moveable ratchet coupling ring 15 is arranged, the ring comprising a proximally facing ratchet surface adapted to engage the distally facing ratchet surface and comprising the same number of teeth, i.e. 24, and a distally facing ratchet surface adapted to engage the proximally facing ratchet surface and comprising the same number of teeth, i.e. 48. A spring 16 provides a biasing distally directed force on the ratchet member thereby forcing the ratchet surfaces into engagement. The ratchet coupling ring 15 and the neighbouring portions of the ratchet member 12 and the stationary ratchet ring 14 are each provided with a plurality of circumferentially and equidistantly arranged axially oriented spline protrusions 17, the protrusions allowing the three ratchet parts to engage a correspondingly configured coupling member 18 in a splined relationship, see below.

Figure 2:
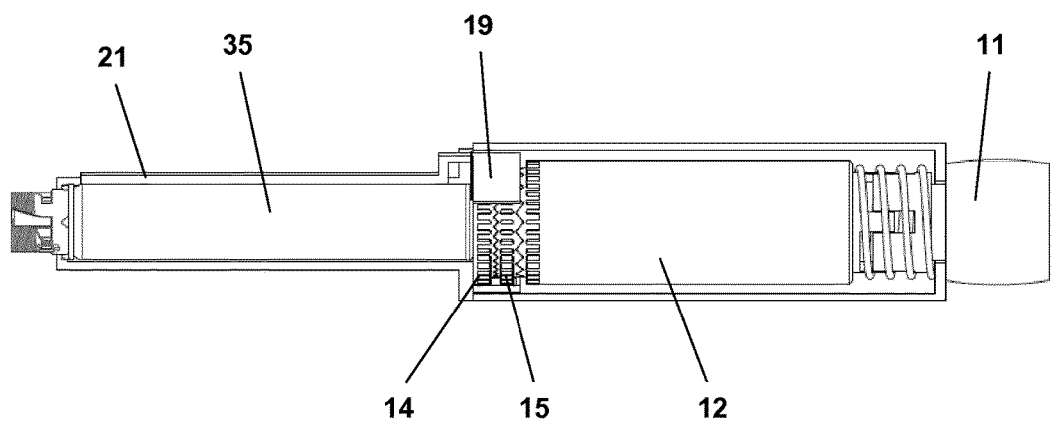
FIGS. 2 and 3 show the device of FIG. 1 with first and second cartridges inserted.
Figure 3:
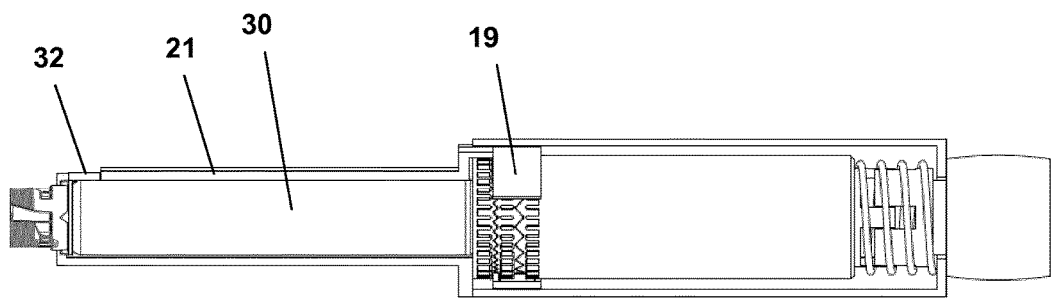
Figure 4:
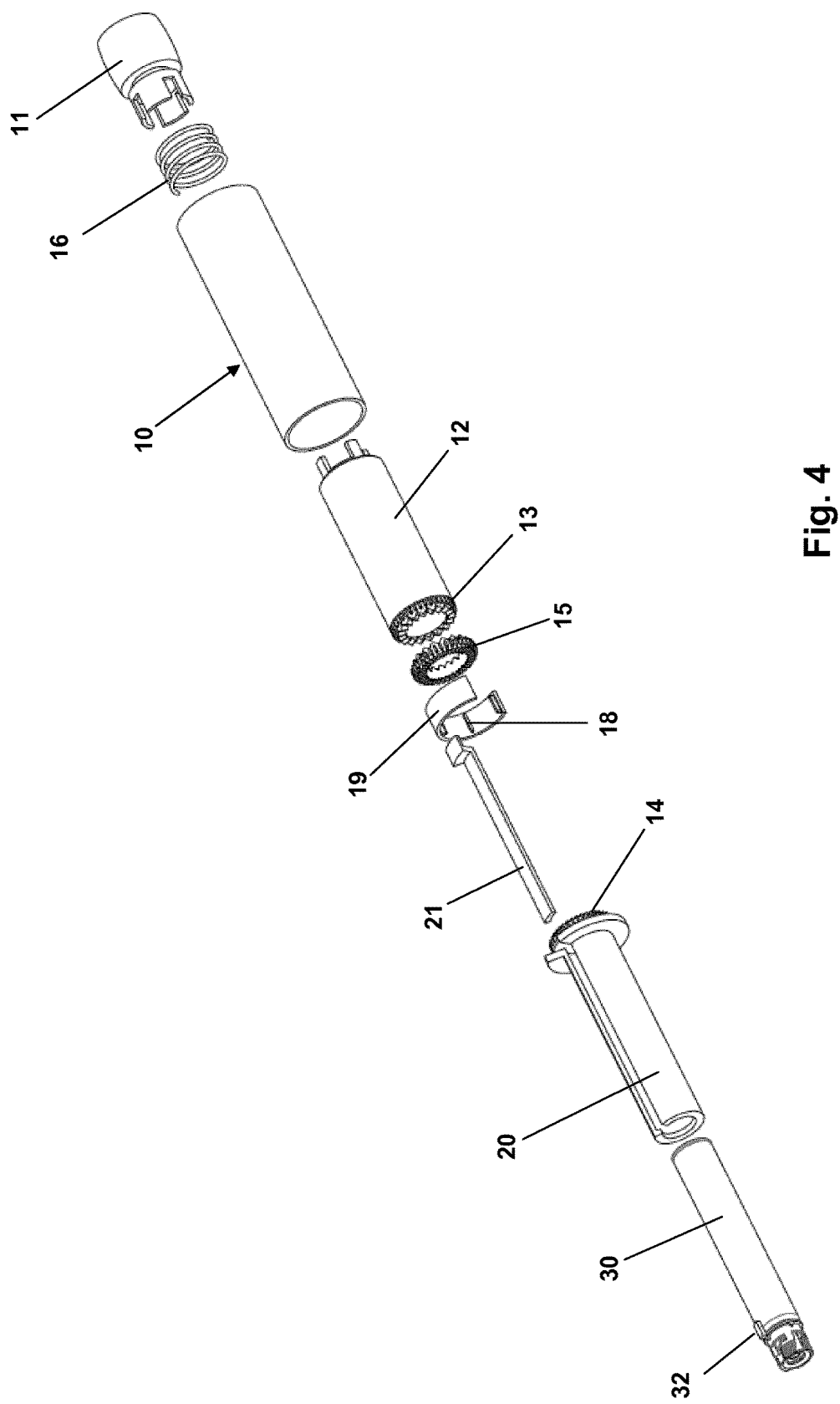
FIG. 4 shows an exploded view of the device of FIG. 1.

The ratchet mechanism comprises a coupling in the form of coupling member 19 which can be actuated between two states by an identifier in the form of a protrusion provided on a cartridge. More specifically, an axially moveable coupling actuator 21 comprises a distal part housed in the cartridge holder and adapted to engage an identifier of an inserted cartridge, and a proximal part 22 adapted to actuate the coupling member between its two positions. Alternatively, the identifier could be arranged at the proximal end of the cartridge, this avoiding the need for a (long) coupling actuator. The coupling member is in the form of a ring (or a partial ring as shown), see FIGS. 2 and 3, in engagement with the ratchet mechanism via a number of spline protrusions 18, see FIG. 4, arranged on the interior surface of the ring. A spring (not shown) provides a distal biasing force on the coupling member. The coupling member is moveable between a distal-most position (urged by the biasing means) corresponding to a first state, and a proximal-most position corresponding to a second state. In the first state the coupling member is in engagement with the stationary ring and the coupling ring, this allowing the opposed ratchet surfaces of the ratchet member 12 and the ratchet coupling ring 15 to interact, e.g. providing a "24 click per rotation" sound as the ratchet member is rotated relative to the now stationary coupling ring. In the second state as shown in FIG. 1 the coupling member is in engagement with the coupling ring and the ratchet member, this allowing the opposed ratchet surfaces of the coupling ring and the stationary ring 14 to interact, e.g. providing a "48 click per rotation" sound as the ratchet member, and thus the ratchet ring, is rotated relative to the stationary ring 14. In this way the dose can be set in increments corresponding to the loaded drug cartridge. As the click sounds correspond to the increments the user is given a corresponding feedback, e.g. one click equals one IU of insulin—albeit with a different amount of rotation.

As described above, axial movement of the coupling ring is controlled by an identifier on the cartridge via the coupling actuator. In the shown embodiment the cartridge 35 of FIG. 2 comprises a 100 IU/ml insulin formulation and the cartridge 30 of FIG. 3 comprises a 200 IU/ml insulin formulation. Whereas the 200 IU cartridge has a "positive" identifier 32 which moves the coupling ring and thus results in the coupling being set from its first to its second state, then the 100 IU cartridge has a "none" identifier which does not move the coupling ring when inserted. However, in the context of the present invention, such a "none" identifier is considered an identifier (corresponding to the value zero being considered a number), just as the coupling is set in its first state although the coupling physically remains in its initial state corresponding to no cartridge being inserted.

Most fully or partly mechanical drug delivery devices have display means adapted to display a drug dose amount (e.g. IU of insulin or mg of growth hormone) in the same fixed increments for each of the first and second drug formulations.

For example, the dose setting means may comprise a rotatable scale drum with indices printed thereon corresponding to the fixed increments in which the dose setting means is settable, e.g. 1 IU. However, if the same scale was used for the above-described device then 1 IU would correspond to two increments and thus to the double amount of active drug. Correspondingly, for such a scale drum the amount of rotation per increment should vary according to the set state, e.g. 24 IU and 48 IU respectively for a full 360 rotation of the dose setting member 11. This could be achieved in a number of ways, e.g. the scale could have two scales printed thereon, the first scale being viewable when the expelling means is in the first state, and the second scale being viewable when the expelling means is in the second state. Which scale is visible could be controlled by means of a moveable window having first and second positions corresponding to the set state of the device. For example, such a window may be controlled by the same means controlling the above-described coupling ring.

Alternatively, the drug delivery device may comprise a processor, electronically controlled display means, and encoder means operationally coupled to the dose setting member, wherein the encoder means is set in a first state by means of the first identifier when a first cartridge is mounted, and the encoder means is set in a second state by means of the second identifier when a second cartridge is mounted, whereby a set drug dose amount is displayed in the same fixed increments for each of the first and second drug formulations. By this arrangement the display is not mechanically coupled to the dose setting mechanism, however, the user is provided with mechanical feedback by the ratchet click sounds with one "click" corresponding to 1 IU of insulin irrespective of the type of cartridge loaded.

For the above-described embodiment the encoder may be of the rotational type having a resolution of 360 degrees/48=7.5 degrees, such that one encoder step in the second state corresponds to one increment and thus 1 IU of insulin, and two encoder steps in the first state also correspond to one increment and thus 1 IU of insulin.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery system, comprising:
    a first reservoir unit comprising:
        a first drug formulation of a given drug having a first concentration, and
        a first mechanical identifier corresponding to the first drug formulation,
    a second reservoir unit comprising:
        a second drug formulation of the given drug having a second concentration, and
        a second mechanical identifier corresponding to the second drug formulation,
    a main unit comprising:
        mounting structure allowing either of the first and second reservoir units to be mounted relative to the main unit,
        drug expelling structure for expelling drug from a mounted reservoir unit corresponding to a set dose size, the drug expelling means comprising:
        dose setting structure comprising a rotational dose setting member allowing a user to set a desired dose size for the given drug, the dose size being set in fixed increments for a given state,
    wherein the drug expelling structure has a first state in which an increment corresponds to a first amount of angular displacement of the dose setting member corresponding to a first volume of drug,
    wherein the drug expelling structure has a second state in which an increment corresponds to a second amount of angular displacement of the dose setting member corresponding to a second volume of drug,
    wherein the first amount of angular displacement is different from the second amount of angular displacement, and
    wherein the drug expelling structure is set in the first state by structure of the first identifier when a first reservoir unit is mounted, and the drug expelling structure is set in the second state by structure of the second identifier when a second reservoir unit is mounted.

2. A drug delivery system as in claim 1, wherein the increments of the first and second states correspond to the first and second concentration of drug, whereby for a given number of increments the same amount of drug is expelled.

3. A drug delivery system as in claim 1, wherein the dose setting structure comprises a ratchet mechanism settable in the first and second fixed increments.

4. A drug delivery system as in claim 3, wherein the ratchet mechanism has a first and a second state corresponding to the first and second state of the expelling mechanism.

5. A drug delivery system as in claim 4, wherein the ratchet mechanism comprises:
    a first ratchet ring having a first increment size,
    a second ratchet ring having a second increment size,
    a coupling ring having a first ratchet portion facing the first ratchet ring and having the first increment size, and a second ratchet portion facing the second ratchet ring and having the second increment size,
    a coupling structure having a first and a second state corresponding to the first and second state of the expelling mechanism,
    wherein the coupling ring and the second ratchet ring is rotationally locked to each other in the first state, this providing a ratchet having the first increment size, and
    wherein the coupling ring and the first ratchet ring is rotationally locked to each other in the second state, this providing a ratchet having the second increment size.

6. A drug delivery system as in claim 1, further comprising a display structure adapted to display a drug dose amount in the same fixed increments for each of the first and second drug formulations.

7. A drug delivery system as in claim 6, wherein the dose setting member is operationally coupled to the display structure in the form of first and second rotatable scales, the first scale being viewable when the expelling structure is in the first state, and the second scale being viewable when the expelling structure is in the second state.

8. A drug delivery system as in claim 7, wherein the display structure comprises a rotatable drum member operationally coupled to the dose setting member, the first and second scale being arranged on the drum member.

9. A drug delivery system as in claim 6, wherein the display structure comprises:
    processor structure,
    electronically controlled display structure, and
    encoder structure operationally coupled to the dose setting member,
    wherein the encoder structure is set in a first state by structure of the first identifier when a first reservoir unit is mounted, and the encoder structure is set in a second state by structure of the second identifier when a second reservoir unit is mounted,
    whereby a set drug dose amount is displayed in the same fixed increments for each of the first and second drug formulations.

10. A drug delivery system as in claim 1, the main unit further comprising signal generating structure adapted to generate for a given state a tactile and/or audible signal for each increment during setting of a dose.

11. A drug delivery system as in claim 1, wherein the drug expelling structure are driven manually, by a manually actuated spring, or a pre-energized spring.

* * * * *